US011410757B2

(12) United States Patent
Li et al.

(10) Patent No.: US 11,410,757 B2
(45) Date of Patent: Aug. 9, 2022

(54) FACILITATING HEALTH INTERVENTION SUGGESTION FOR DISEASE MITIGATION AND/OR PREVENTION

(71) Applicant: International Business Machines Corporation, Armonk, NY (US)

(72) Inventors: Xiang Li, Beijing (CN); Hai Feng Liu, Beijing (CN); Guo Tong Xie, Xi Er Qi (CN); Yi Qin Yu, Beijing (CN); Ping Zhang, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 255 days.

(21) Appl. No.: 15/797,295

(22) Filed: Oct. 30, 2017

(65) Prior Publication Data
US 2019/0130069 A1    May 2, 2019

(51) Int. Cl.
*G16H 10/60* (2018.01)
*G16H 50/30* (2018.01)
*G16H 50/20* (2018.01)
*G06N 20/00* (2019.01)
*G16H 20/60* (2018.01)
*G16H 20/30* (2018.01)
*G16H 20/00* (2018.01)

(52) U.S. Cl.
CPC .............. *G16H 10/60* (2018.01); *G06N 20/00* (2019.01); *G16H 20/00* (2018.01); *G16H 20/30* (2018.01); *G16H 20/60* (2018.01); *G16H 50/20* (2018.01); *G16H 50/30* (2018.01)

(58) Field of Classification Search
CPC ........ G16H 10/60; G16H 20/60; G16H 20/00; G16H 20/30; G16H 50/30; G16H 50/20; G06N 20/00; G06N 5/022
See application file for complete search history.

(56) References Cited

U.S. PATENT DOCUMENTS

| 8,521,546 B2 | 8/2013 | Brown |
| 9,536,052 B2 | 1/2017 | Amarasingham et al. |
| 2002/0107707 A1 | 8/2002 | Naparstek et al. |

(Continued)

OTHER PUBLICATIONS

Sun, et al., "LINKAGE: An Approach for Comprehensive Risk Prediction for Care Management," Last Accessed Sep. 13, 2017, 10 pages.

(Continued)

*Primary Examiner* — Gregory D. Moseley
(74) *Attorney, Agent, or Firm* — Amin, Turocy & Watson, LLP

(57) ABSTRACT

Systems, computer-implemented methods and/or computer program products that facilitate providing treatment suggestions are described herein. In one example, a computer-implemented method comprises: generating, by a system operatively coupled to a processor, treatment directed graphs associated with a plurality of treatment regimens, wherein, in connection with generating respective treatment directed graphs, penalties are applied during weighting of respective regimens as a function of an associated confidence level; identifying a treatment directed graph that corresponds to the patient directed graph; and outputting a set of treatment suggestions associated with the treatment directed graph that corresponds to the patient directed graph.

17 Claims, 9 Drawing Sheets

(56) References Cited

U.S. PATENT DOCUMENTS

| | | |
|---|---|---|
| 2006/0129427 A1 | 6/2006 | Wennberg |
| 2009/0106004 A1 | 4/2009 | Edwards et al. |
| 2017/0124269 A1* | 5/2017 | McNair .................. G16H 50/20 |
| 2017/0277841 A1* | 9/2017 | Shankar ................ G06F 19/326 |
| 2017/0277857 A1* | 9/2017 | De La Torre ......... G06F 19/324 |
| 2018/0181719 A1* | 6/2018 | Balian ................... G16H 40/20 |

OTHER PUBLICATIONS ibm.com, "Watson for Oncology," Retrieved Aug. 2, 2017, 10 pages.

Zafra-Cabeza, et al., "A Risk-based Model Predictive Control Approach to Adaptive Interventions in Behavioral Health," Proceedings of the 45th IEEE Conference on Decision & Control Manchester Grand Hyatt Hotel San Diego, CA, USA, Dec. 13-15, 2006, 6 pages.

* cited by examiner

FACILITATING HEALTH INTERVENTION SUGGESTION FOR DISEASE MITIGATION AND/OR PREVENTION

BACKGROUND

The subject disclosure relates to facilitating medical treatment, and more specifically, providing a set of treatment suggestions regarding diseases associated with the patient.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments herein, devices, systems, computer-implemented methods, apparatus and/or computer program products that facilitate provisioning information indicative of treatment recommendations.

According to one embodiment, a system is provided. The system can comprise a memory that stores computer executable components. The system can also comprise a processor, operably coupled to the memory, and that can execute computer executable components stored in the memory. The computer executable components can comprise a patient assessment component that generates a patient directed graph regarding two or more diseases associated with a patient. The computer executable components can further comprise a treatment component that generates treatment directed graphs associated with a plurality of treatment regimens, wherein, in connection with generating respective treatment directed graphs, penalties are applied during weighting of respective regimens as a function of an associated confidence level. The computer executable components can further comprise a matching component that identifies a treatment directed graph that corresponds to a patient directed graph. The computer executable components can further comprise a suggestion component that outputs a set of treatment suggestions associated with the treatment directed graph that corresponds to the patient directed graph.

According to another embodiment, a computer-implemented method is provided. The computer-implemented method can comprise generating, by a system operatively coupled to a processor, a patient directed graph regarding two or more diseases associated with a patient. The computer-implemented method can further comprise generating, by the system, treatment directed graphs associated with a plurality of treatment regimens, wherein, in connection with generating respective treatment directed graphs, penalties are applied during weighting of respective regimens as a function of an associated confidence level. The computer-implemented method can further comprise identifying, by the system, a treatment directed graph that corresponds to a patient directed graph. The computer-implemented method can further comprise outputting by the system, a set of treatment suggestions associated with the treatment directed graph that corresponds to the patient directed graph.

According to another embodiment, a computer program product that facilitates provisioning a set of treatment suggestions is provided. The computer program product can comprise a computer readable storage medium having program instructions embodied therewith. The program instructions can be executable by a processor to cause the processor to generate a patient directed graph regarding two or more diseases associated with a patient. The program instructions can further be executable by a processor to cause the processor to generate treatment directed graphs associated with a plurality of treatment regimens, wherein, in connection with generating respective treatment directed graphs, penalties are applied during weighting of respective regimens as a function of an associated confidence level. The program instructions can further be executable by a processor to cause the processor to identify a treatment directed graph that corresponds to a patient directed graph. The program instructions can further be executable by a processor to cause the processor to provide to the patient a set of treatment suggestions associated with the treatment directed graph that corresponds to the patient directed graph.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

One or more embodiments described herein can facilitate provisioning a set of treatment suggestions. In one or more embodiments, treatment suggestions can be used as a treatment plan for medical conditions and/or a health intervention (e.g., disease prevention and/or control) to prevent or remediate two or more diseases. As used herein, the term "health intervention" can be used interchangeably with "treatment plan." Treatment suggestions can help a patient prevent and/or control a set of diseases that share a consistent health domain (e.g., cardiovascular diseases including stroke, myocardial infarction, congestive heart failure, etc.). The treatment suggestions can be predictive in nature, which allow the patient to be aware of the impact between the particular interventional factors (e.g., controllable factors such as diet and exercise) and the target diseases. The predictive relationship, from which the treatment suggestions are generated, can be based on health data and/or guided by knowledge from current published literature in some embodiments.

In one or more embodiments described herein, the use of treatment suggestions and/or health intervention suggestions can help decrease healthcare cost and improve national health. In some embodiments, the treatment suggestions can also minimize experience based suggestions from physicians that can be less expansive than a health suggestion with an up-to-date health database that is continually updated with current published literature. The treatment suggestions can be specific to target diseases while considering quantitative predictive relationships among health factors and diseases. In some embodiments, the treatment suggestions can also convey the manner in which a selected health intervention impacts the diseases. In other words, the treatment suggestions can address multiple diseases associated with a patient, which can result in a more complex treatment regimen since a particular treatment for one disease can have an impact on a treatment of another disease.

Figure 1:
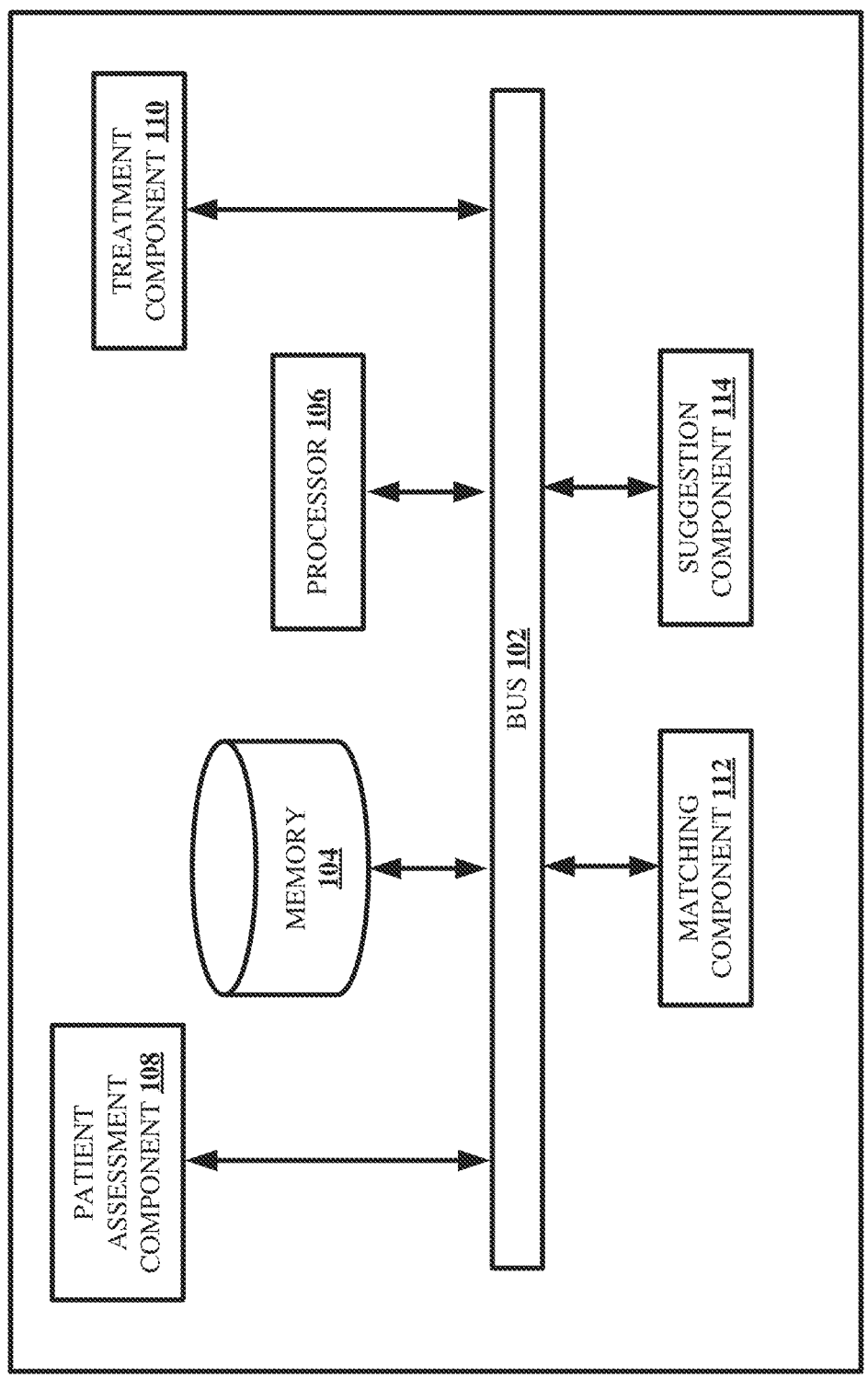
FIG. 1 illustrates a block diagram of an example, non-limiting system facilitating provisioning a set of treatment suggestions in accordance with one or more embodiments described herein.

FIG. 1 illustrates a block diagram of an example, non-limiting system facilitating provisioning a set of treatment suggestions in accordance with one or more embodiments described herein. Aspects of systems (e.g., system 100 and the like), apparatuses or processes explained in this disclosure can constitute one or more machine-executable components embodied within one or more machines, e.g., embodied in one or more computer readable mediums (or media) associated with one or more machines. Such components, when executed by the one or more machines, e.g., computers, computing devices, virtual machines, etc., can cause the machines to perform the operations described.

In various embodiments, the system 100 can be any type of component, machine, device, facility, apparatus, and/or instrument that comprises a processor. In some embodiments, system 100 is capable of effective and/or operative communication with a wired and/or wireless network. Components, machines, apparatuses, devices, facilities, and/or instrumentalities that can comprise the system 100 can include, but are not limited to, tablet computing devices, handheld devices, server class computing machines and/or databases, laptop computers, notebook computers, desktop computers, cell phones, smart phones, consumer appliances and/or instrumentation, industrial and/or commercial devices, digital assistants, multimedia Internet enabled phones, multimedia players, and the like.

As illustrated in FIG. 1, the system 100 can comprise bus 102, memory 104, processor 106, patient assessment component 108, treatment component 110, matching component 112 and/or suggestion component 114. The bus 102 can provide for interconnection of various components of the system 100. The memory 104 and processor 106 can carry out computation and/or storage operations of the system 100 as described herein. It is to be appreciated that in some embodiments one or more system components can communicate wirelessly with other components, through a direct wired connection or integrated on a chipset.

In one or more embodiments described herein, system 100 can employ predictive analytics to automatically generate treatment suggestions. For example, the automatic generation can be based on information retained in a knowledge base. As used herein, the term "knowledge base" can be a database or other storage location or repository that can store one or more types of information. All such embodiments are envisaged.

The knowledge base can comprise information related to one or more health data. In some embodiments, the information related to the one or more health data can be gathered over time and retained in the knowledge base. In some embodiments, the information gathered can include quantitative predictive relationships among health factors and diseases. Based on the obtained information, the system 100 can evaluate the knowledge base (or multiple knowledge bases) and generate one or more patterns and/or can graph information known about a user's health profile (e.g., a patient's health profile) to the information known about other health data. The predictive analytics of system 100 can determine that, if information of the user's health profile is similar to one or more other health data, the relationships among health factors and diseases can be utilized to automatically generate treatment suggestions.

The computer processing systems, computer-implemented methods, apparatus and/or computer program products described herein can employ hardware and/or software to generate treatment suggestions that are highly technical in nature, that are not abstract and that cannot be performed as a set of mental acts by a human. For example, the one or more embodiments can perform the lengthy interpretation and analysis on the thousands of available literatures to determine which health factors and diseases should be utilized for a user's health profile and to generate treatment suggestions with multiple disease risks. In some embodiments, multiple health factors and diseases can be learned together with other related health factors and diseases. In another example, the one or more embodiments can perform predictive analytics on a large amount of data to automatically facilitate generating treatment suggestions with a high level of accuracy, even in the absence of detailed knowledge about the user's health profile. Treatment suggestions generated for a user's health profile can be stored in a knowledge base to automatically generate treatment suggestions for another user's health profile with similar health factors. Accuracy can be evaluated by comparing a training set with a test set. After training a model employing a training set, accuracy can be calculated using a test set by computing percentage of output generated by the model running on the training set elements that matches a predicted target.

The patient assessment component 108 can generate a patient directed graph regarding two or more diseases associated with a patient. In some embodiments, the patient directed graph can include or indicate patient health profile data. An example patient directed graph can include, but is not limited to, lifestyle and health status data pertaining to age, body mass index, systolic blood pressure, diabetes, atrial fibrillation, heart rate, congestive heart failure, cardiovascular disease, or stroke. The patient assessment component 108 can collect and/or receive health profile data for a patient used by the system to generate the patient directed graph regarding two or more diseases associated with a patient. The health profile data can be received from a number of sources such as a self-assessment (e.g., ache, pain, nausea, headache, etc.) provided by the patient and/or entered into a medical database by a medical professional, lab results, physical exams, past medical history, etc.

The patient assessment component 108 can identify the health profile data used by the system 100 to generate the patient directed graph regarding the two or more diseases associated with the patient. The patient assessment component 108 can identify the health profile data of the patient by analyzing health factors that can have a health impact. For example, information as to whether a patient smokes can be valuable data for a patient that is at risk for cardiovascular disease. A health profile data can be applied to a treatment directed graph to generate a patient directed graph, which can be viewed as an instance of the treatment directed graph. A patient directed graph can be matched to a treatment directed graph to generate treatment suggestions specific to the diseases that the patient has or can be at risk of having. A patient directed graph can be matched to a treatment directed graph by finding a treatment directed graph that has the same health factors found on a patient directed graph. A treatment directed graph, however, can indicate a number of potential diseases relating to a set of a patient's health factors so that treatment suggestions can be generated to prevent and/or mitigate the likelihood of the potential diseases or health risks.

The treatment component 110 can generate treatment directed graphs associated with a plurality of treatment regimens. Treatment suggestions or treatment regimens can be based on predictive relationships between health factors and diseases and between diseases. For example, if the treatment component 110 indicates that the predictive relationships show that smoking, body mass index and atrial fibrillation increases the risk of stroke and congestive heart failure, the treatment component 110 can output treatment regimens or treatment suggestion that can include quit smoking and start exercising if the patient is someone who smokes and/or has had atrial fibrillation. The treatment component 110 can receive structured health data and predictive relationships relating to diseases from literature used by the system to generate the treatment directed graphs associated with the plurality of treatment regimens. Predictive relationships can be extracted by the treatment component 110 by analyzing literature and/or determining how different health factors are associated or related to one another or to other diseases. In some embodiments, the structured health data can be known health data relating to a multitude of diseases that are organized in defined fields. The predictive relationships relating to diseases from literature can be health data extracted from literature, which can describe the effects between health factors and diseases and between diseases. Predictive relationship extraction of diseases from current literature by the treatment component 110 can enable the system 100 to be current with the latest research studies, and/or a more accurate treatment directed graph can be generated for a multitude of diseases.

In connection with generating respective treatment directed graphs, penalties can be applied during weighting of respective regimens as a function of an associated confidence level. The penalties can be calculated by using a set of formulas as described below. After a training process, a treatment directed graph can be generated with all known weight values "$w_{ij}$" (e.g., "w" stands for the weight value or penalty, "I" stands for the initial starting node and "j" stands for the pointed node or end node). The corresponding model will be expression Y=f(X, W). This is the model of relationship among factors X and target diseases Y. The weight values can be applied to the treatment directed graph to generate a patient directed graph, which can be treated as an instance of the treatment directed graph.

A predictive relationship between a health factor or disease with the other diseases can be extracted from analyzing literature. The relationship can have a positive or negative impact between health factors and diseases or among diseases. For example, smoking (e.g., a health factor) can be considered to have a direct positive impact on stroke (e.g., a disease), which means smoking can increase the risk of having a stroke. A negative impact decreases the risk of a disease. A disease can also be a health factor to another disease. For example, atrial fibrillation (e.g., a disease) can be a health factor that can increase the risk of getting a stroke (e.g., a disease).

Once a set of treatment directed graphs are generated (e.g., from structured health data and from respective literature), the patient directed graph can be matched with a treatment directed graph generated by the treatment component 110. One or more treatment suggestions can be generated in connection with the treatment directed graph that corresponds to treating the plurality of diseases associated with the patient. Treatment suggestions can be generated by using known weight values to calculate the risk score for one or more target diseases.

The matching component 112 can identify a treatment directed graph that corresponds to a patient directed graph. For example, for a patient with a defined set of health factors on the patient directed graph, the matching component 112 can have as a treatment directed graph the set of health factors on the patient directed graph in addition to potential risk for other related diseases. The matching of a patient directed graph with a treatment directed graph by the matching component 112 can be based on generated treatment directed graphs stored in the knowledge base. The health factors and known diseases on a patient directed graph can be matched, by the matching component 112, with a treatment directed graph so an accurate set of treatment protocols or treatment suggestions can be determined.

The treatment component 110 can generate treatment directed graphs by graphing predictive relationships between health factors and diseases based on literature. The suggestion component 114 can output one or more (or, in some embodiments, a set of) treatment suggestions associated with the treatment directed graph that corresponds to the patient directed graph. In various embodiments, the suggestion component 114 can output the treatment suggestions to a patient, a machine, a database or any other human or machine entity. For example, the treatment suggestions can include health factors that can help control the risk of getting certain diseases. The treatment suggestions can include health factors that are controllable versus factors that are not controllable and how much impact each health factor (or, in some embodiments, one or more health factors) has on a disease. Examples of health factors that are not controllable (e.g., uncontrollable factors or un-interventional factors) can include age, blood type, etc., because these factors cannot be changed. Health factors that are controllable (e.g., controllable factors or interventional factors) can include smoking practice, exercising practice, body mass index, etc., because these factors can be changed.

Figure 2:
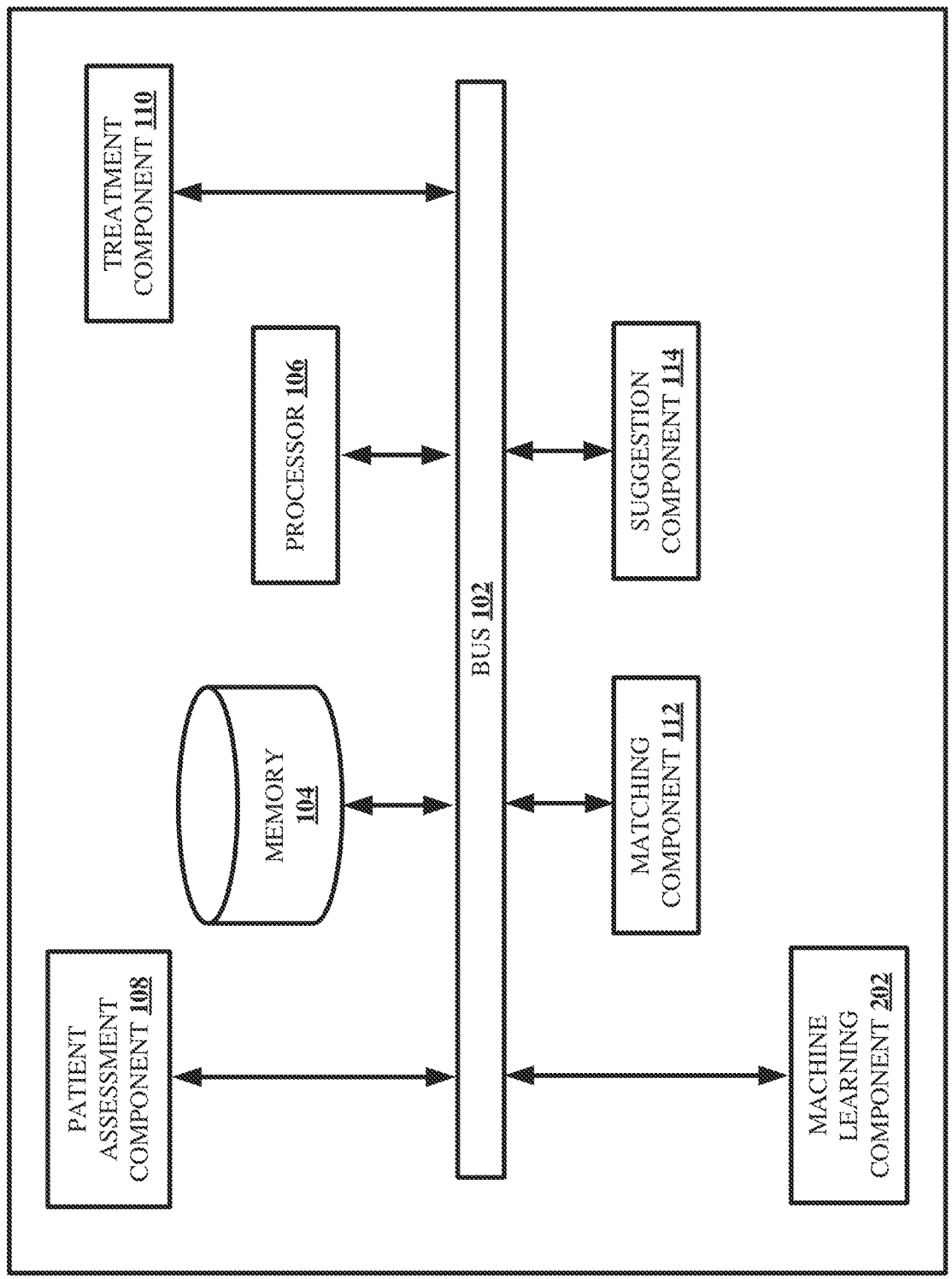
FIG. 2 illustrates a block diagram of an example, non-limiting system facilitating provisioning a set of treatment suggestions including a machine learning component in accordance with one or more embodiments described herein.

FIG. 2 illustrates a block diagram of an example, non-limiting system facilitating provisioning a set of treatment suggestions including a machine learning component 202 in accordance with one or more embodiments described herein. Repetitive description of like elements employed in other embodiments described herein is omitted for sake of brevity.

The machine learning component 202 can extract the predictive relationships relating to diseases from literature. The predictive relationships relating to diseases from literature can have an associated weighted value. The machine learning component 202 can analyze literature to determine whether a health factor has a predictive relationship with another health factor or another disease. A first penalty value can be assigned based on whether there is a predictive relationship between a health factor and a disease. A second penalty value can be assigned based on whether the health factor has a positive or negative impact on the disease. For example, the machine learning component can extract from literature that atrial fibrillation has a positive impact on stroke, which increases the risk of stroke. The first penalty, controlled by Matrix A (e.g., see FIG. 7 below), can be 0 because there is a predictive relationship between atrial fibrillation and stroke. More specifically, because there is a relationship between atrial fibrillation and stroke, the weight between the nodes that represent atrial fibrillation and stroke during the training will not be penalized. If there is no predictive relationship, the penalty is a 1, which also indicates that the weight value is penalized. The second penalty, controlled by Matrix B (e.g., see FIG. 7 below), can be +1 because there is a positive relationship to indicate that atrial fibrillation increases the risk of stroke. A negative relationship indicated by a −1 shows that a health factor decreases the risk of a disease. If there is no relationship, a 0 is assigned. A penalty can be assigned to the impact relationship in order to converge on a holistic treatment regimen and generate a more accurate set of treatment protocols (e.g., treatment suggestions). A first and a second penalty are assigned based on a set of formulas described below. The machine learning component 202 can learn the predictive relationships relating to diseases from literature, individually and concurrently in time by utilizing multi-task learning because a patient's health conditions is complex and a specific health risk can be associated with other related risks from other health domains. Multi-task learning can be utilized to learn a disease together with other diseases, each at a time or all at the same time to enable learning predictive relationships for diseases having risk factors that can affect other diseases.

Figure 3:
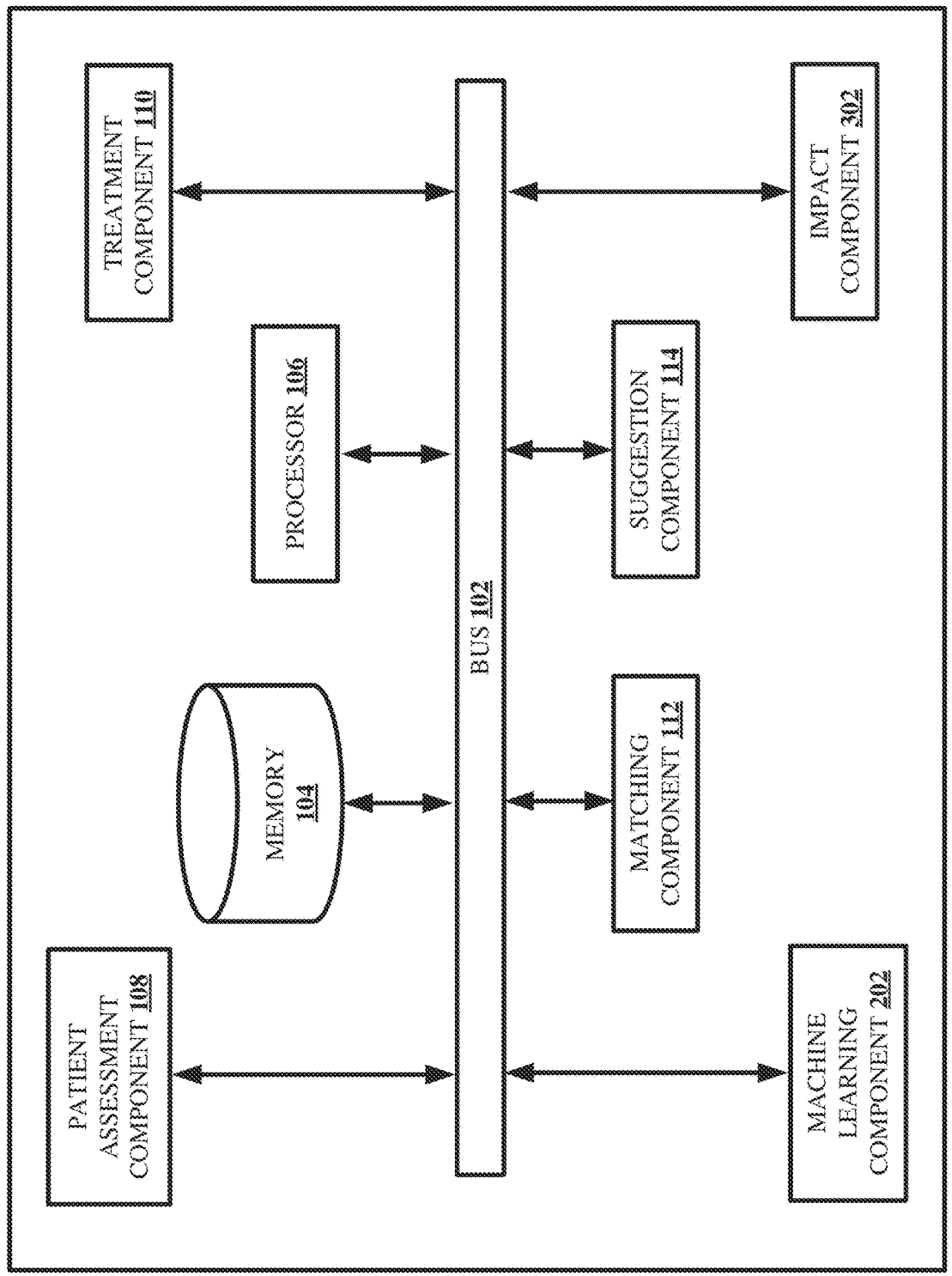
FIG. 3 illustrates a block diagram of an example, non-limiting system facilitating provisioning a set of treatment suggestions including an impact component in accordance with one or more embodiments described herein.

FIG. 3 illustrates a block diagram of an example, non-limiting system facilitating provisioning a set of treatment suggestions including impact component 302 in accordance with one or more embodiments described herein. Repetitive description of like elements employed in other embodiments described herein is omitted for sake of brevity.

The impact component 302 can apply the patient directed graph to the treatment directed graph to identify one or more risk factors, one or more controllable factors or one or more uncontrollable factors. A treatment directed graph can be selected for a patient with health factors on the patient directed graph, which can be treated as an instance of the treatment directed graph. The treatment directed graph, however, can include risk factors or diseases that the patient can eventually have if treatment or preventive measures are not taken. For example, for a patient who has a patient directed graph that includes diabetes and high systolic blood pressure, a treatment directed graph can be selected to include diabetes and systolic blood pressure as health factors or risk factors. A treatment directed graph that includes systolic blood pressure and diabetes as risk factors can include treatment suggestions for atrial fibrillation, which have predictive relationships with systolic blood pressure and diabetes. A high systolic blood pressure is a risk factor that can be a controllable factor in preventing atrial fibrillation with a proper diet and exercise to keep the numbers down at a healthy range. Diabetes is a risk factor that can be either a controllable factor or an uncontrollable factor in preventing atrial fibrillation. Type 1 diabetes can be an uncontrollable factor in preventing atrial fibrillation because there is no known cure for type 1 diabetes. Type 2 diabetes can be a controllable factor because type 2 diabetes can be reversed with lifestyle changes. The risk factors can be tagged or marked as a controllable factor or an uncontrollable factor. All the controllable factors can be found based on whether the controllable factors can be maintained at a level that do not have a negative health implications. After the controllable factors are found, the impact component 302 can calculate the impact of the controllable factors by employing the weight values of the controllable factors (e.g., health factors, risk factors, etc.) to calculate the risk score for the target diseases.

Together, the components of systems 100, 200 and/or 300 can communicate with one another to generate treatment suggestions and/or collect the information learned through the process for future use. The treatment component 110 can collect structured health data and predictive relationships relating to diseases from literature (e.g., extracted from literature via the machine learning component 202) to generate the treatment directed graph. The machine learning component 202 can also provide weight values to confidence level with respect to efficacy of treatment for the diseases. The matching component 112 can match the patient directed graph (e.g., generated via the patient assessment component 108) to the treatment directed graph (e.g., generated via the treatment component 110). The impact component 302 can apply the patient directed graph to the treatment directed graph to identify risk factors as controllable factors or uncontrollable factors. The impact component 302 can calculate an impact of the controllable factors by estimating the quantitative causal probabilities from controllable factors to risk factors. The suggestion component 114 can provide the patient a set of treatment suggestions based on the treatment directed graph that corresponds with the patient directed graph and the impact of the controllable factors for the risks. The treatment suggestions that the patient receives is a comprehensive health intervention suggestion with health factors to control the risk of getting diseases or remediate existing diseases and efficacy of treatment (e.g., how much risk will be decreased with treatment).

Figure 4:
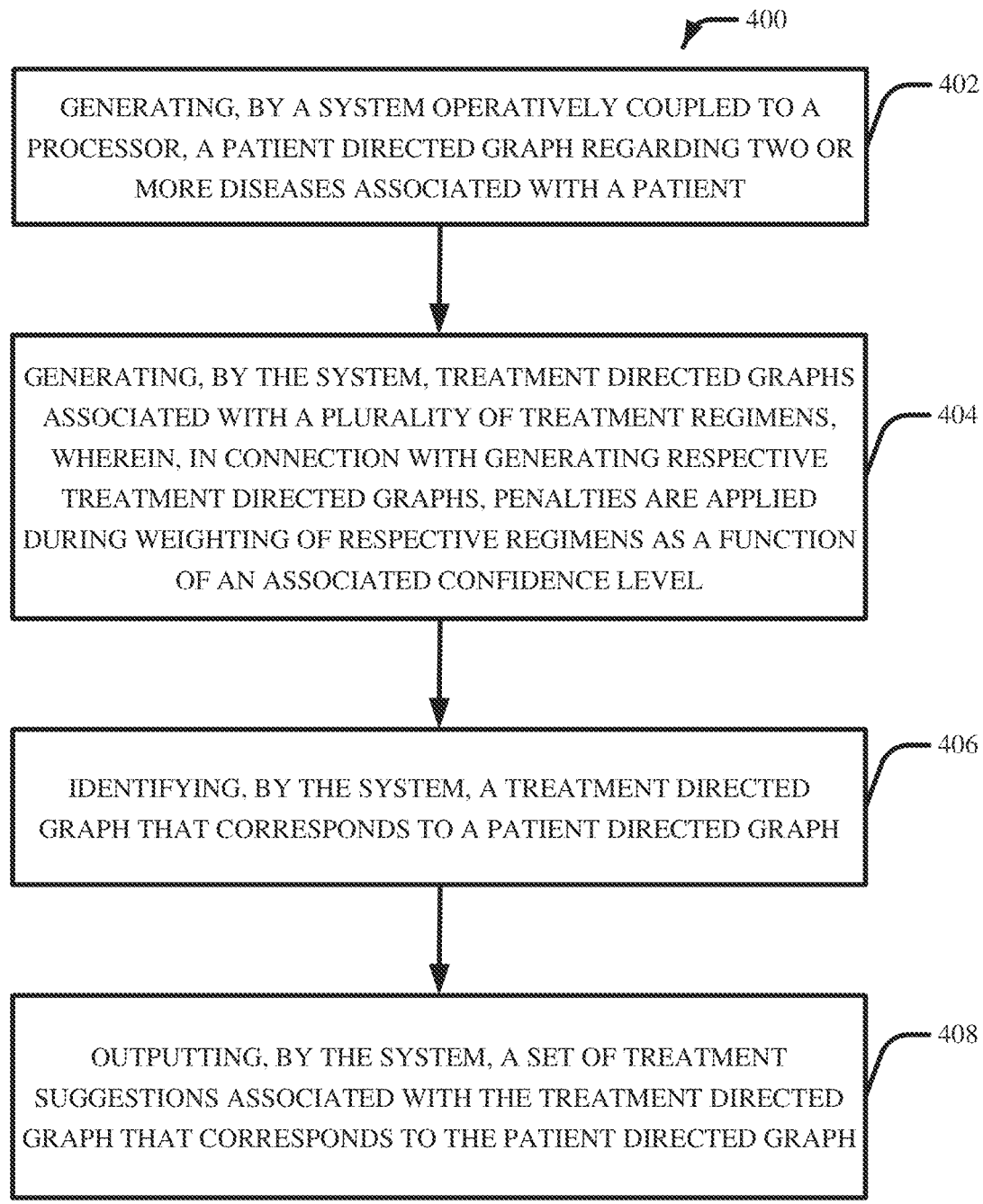
FIG. 4 illustrates a flow diagram of an example, non-limiting computer-implemented method facilitating provisioning a set of treatment suggestions in accordance with one or more embodiments described herein.

FIG. 4 illustrates a flow diagram of an example, non-limiting computer-implemented method 400 that can facilitate provisioning a set of treatment suggestions in accordance with one or more embodiments described herein. Repetitive description of like elements employed in other embodiments described herein is omitted for sake of brevity.

At 402, the computer-implemented method can comprise generating, by a system operatively coupled to a processor, a patient directed graph (e.g., via the patient assessment component 108) regarding two or more diseases associated with a patient. At 404, the computer-implemented method can comprise generating, by the system, treatment directed graphs (e.g., via the treatment component 110) associated with a plurality of treatment regimens, wherein, in connection with generating respective treatment directed graphs, penalties are applied during weighting of respective regimens as a function of confidence level associated therewith. At 406, the computer-implemented method can comprise identifying, by the system, a treatment directed graph (e.g., via the matching component 112) that corresponds to a patient directed graph. At 408, the computer-implemented method can comprise outputting, by the system, a set of treatment suggestions (e.g., via the suggestion component 114) associated with the treatment directed graph that corresponds to the patient directed graph. In some embodiments, the set of treatment suggestions can be output to a patient, a caregiver, a machine, a computer or any other entity.

Figure 5:
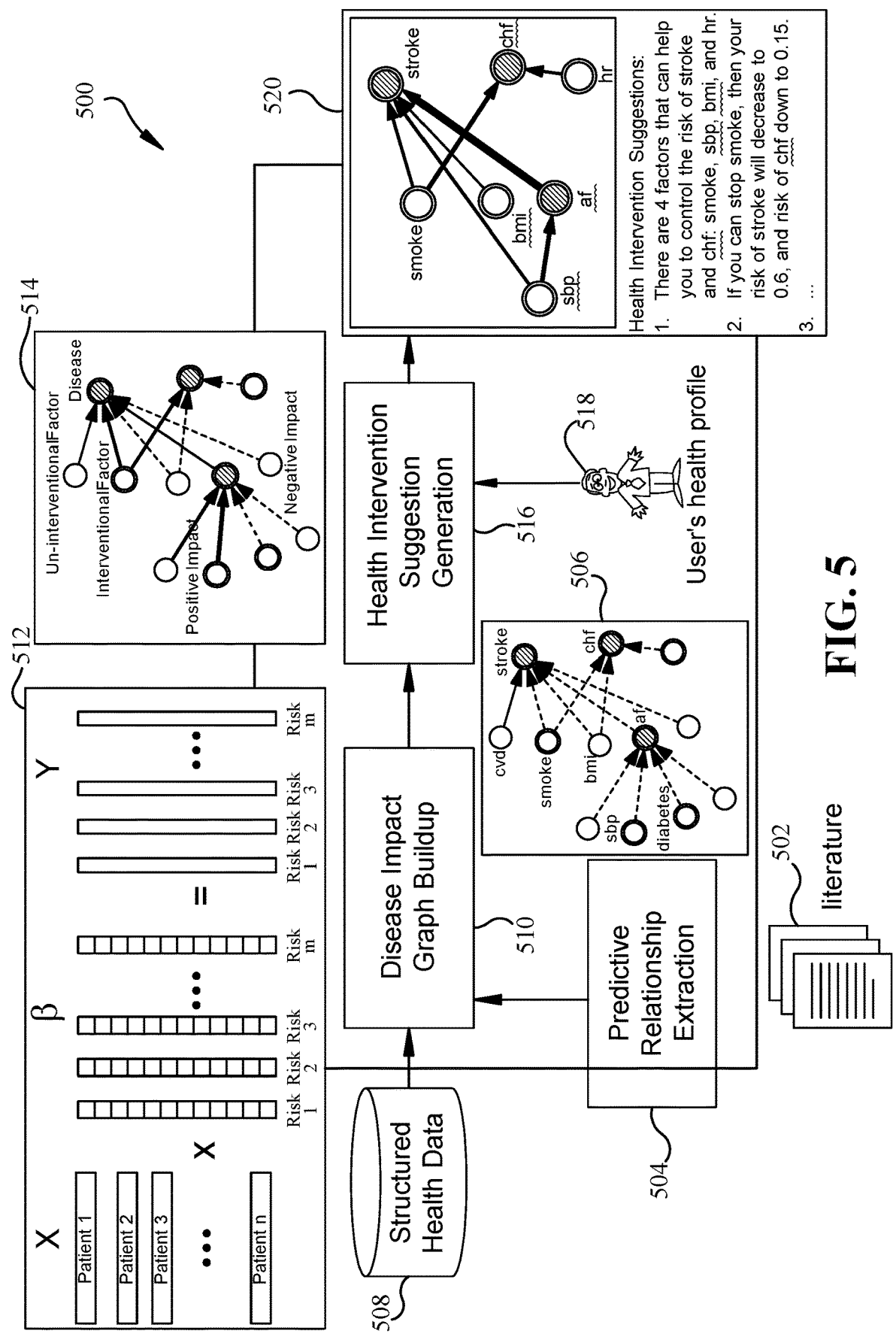
FIG. 5 illustrates a block diagram of an example, non-limiting system workflow facilitating provisioning a set of treatment suggestions in accordance with one or more embodiments described herein.

FIG. 5 illustrates a block diagram of an example, non-limiting system workflow 500 in accordance with one or more embodiments described herein. The machine learning component 202 can extract predictive relationships (e.g., the predictive relationship extraction 504) relating to diseases from the literature 502, which is shown in the directed graph 506 with edges (e.g., lines) connecting the health factors and diseases that has an impact on one another. A weighted value to confidence level with respect to efficacy of treatment for the disease can be allocated by the machine learning component 202 by employing a multi-task learning mechanism. The disease impact graph buildup 510 (e.g., the treatment component 110) can receive as input the predictive relationship extraction 504 with weighted value and the structured health data 508 to generate the treatment directed graph 514. The matching component 112 can identify the treatment directed graph that corresponds to the patient directed graph or user's health profile 518 (e.g., via the patient assessment component 108). The impact component 302 can apply the user's health profile 518 to the treatment directed graph 514 to identify risk factors as controllable factors or uncontrollable factors and calculate the impact of the controllable factors (e.g., risk score for the target diseases). The health intervention suggestion generation 516 (e.g., the suggestion component 114) can provide the patient with the treatment suggestions 520 based on the treatment directed graph 514 that corresponds with the user's health profile 518 and the impact of the controllable factors for the risks.

Figure 6:
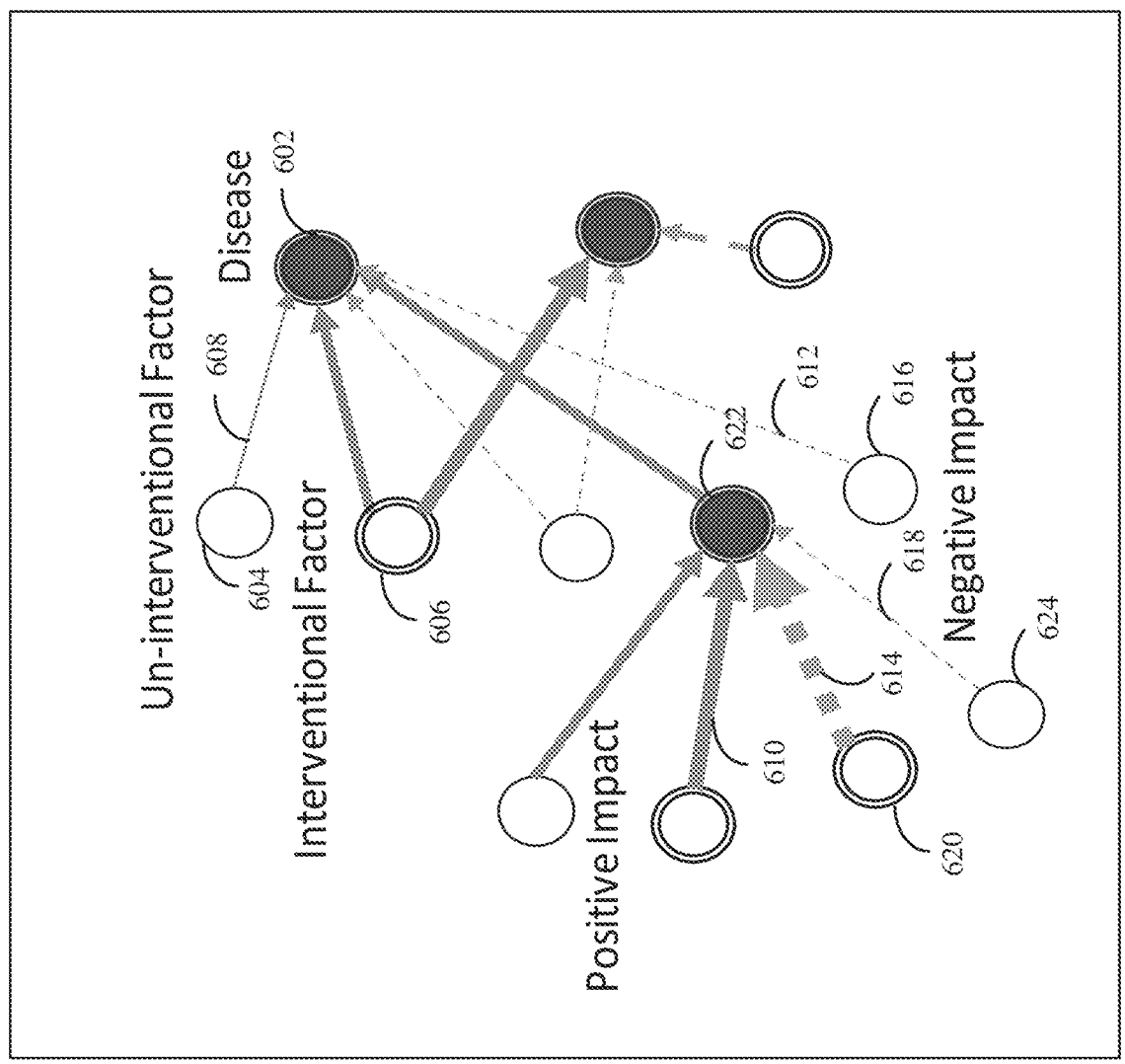
FIG. 6 illustrates a block diagram of an example, non-limiting treatment directed graph facilitating provisioning a set of treatment suggestions in accordance with one or more embodiments described herein.

FIG. 6 illustrates a block diagram of an example, non-limiting treatment directed graph 600 in accordance with one or more embodiments described herein. The treatment directed graph 600 is a graph that can store quantitative predictive relationships among health factors and selected diseases. The treatment directed graph 600 is illustrated here with thin and thick, solid lines; thin and thick, dashed lines; single-ringed and double-ringed, white circles; and darkened circles. It can be appreciated that the treatment directed graph 600 can take a different form, pattern or shade. As shown here, the darkened nodes (e.g., the darkened circles) such as node 602 indicate a disease. The single-ringed, white nodes such as node 604 are un-interventional factors (e.g., uncontrollable factors or uncontrollable health factors). The double-ringed, white nodes such as node 606 are interventional factors (e.g., controllable factors or controllable health factors). Solid edges (e.g., solid lines) such as edge 608 and edge 610 indicate positive impact in the direction of the arrows. For example, node 606 is an interventional or controllable factor that has a positive impact on node 602 (e.g., a disease). Dashed edges (e.g., dashed lines) such as edge 612 and edge 614 indicate negative impact in the direction of the arrows. For example, node 616 is an un-interventional factor or uncontrollable factor that has a negative impact on node 602 (e.g., a disease). The thicker the edges or lines, the larger the impact is on the disease as pointed by the arrows. For example, edge 614 is thicker than edge 618, therefore, indicates that node 620 (e.g., a controllable health factor) has a larger impact on node 622 (e.g., a disease) than node 624 (e.g., an uncontrollable health factor) on node 622.

Figure 7:
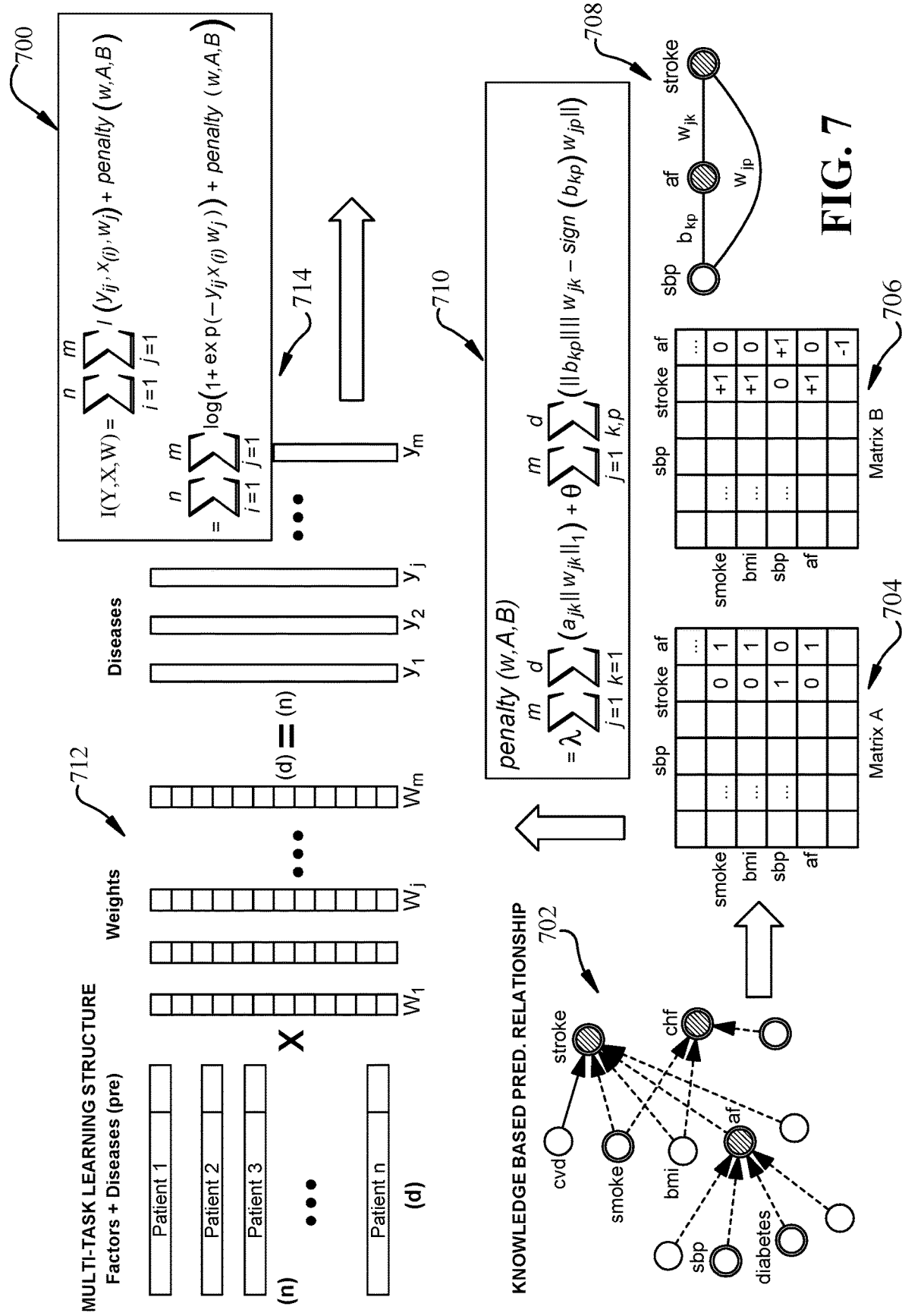
FIG. 7 illustrates a block diagram of an example, non-limiting multi-task learning system that incorporates predictive relationships relating to diseases from literature in accordance with one or more embodiments described herein.

FIG. 7 illustrates a block diagram of an example, non-limiting multi-task learning structure 700, employed by the machine learning component 202, that incorporates predictive relationships relating to diseases from literature (e.g., knowledge based predictive relationship) in accordance with one or more embodiments described herein. A set of clinical papers are collected and predictive relationships in the clinical papers are extracted. For example, a paper that predicts the occurrence of stroke can include risk factors such as atrial fibrillation, age, etc., and the predictive relationships between stroke and the risk factors are applied to build the initial directed graph such as initial directed graph 702. The initial directed graph 702 can include edges (e.g., lines) connecting the nodes, which represents health factors and diseases, to indicate the existence of a relationship or predictive relationship between the nodes (e.g., health factors and diseases or among diseases). As a non-limiting example, the initial directed graph 702 has as nodes, cvd (cardiovascular disease), stroke, smoke, bmi (body mass index), chf (congestive heart failure), sbp (systolic blood pressure), af (atrial fibrillation) and diabetes. The initial directed graph 702 can be analyzed by charting matrices such as here in Matrix A (e.g., matrix 704) and Matrix B (e.g., matrix 706) to calculate the a first and a second penalty for the predictive relationships. The matrices are two-dimensional with the nodes labeled on the x and y axes. In Matrix A (e.g., matrix 704), the block that represents two nodes can receive a 0 if there is a relationship (e.g., has a connecting line between the nodes) or a 1 if there is no relationship. For example, the block that represents the nodes going from smoke to stroke has a 0 because there is a line connecting the nodes. However, the block that represents the nodes going from sbp to stroke has a 1 because there are no lines connecting the nodes.

In Matrix B (e.g., matrix 706), the block that represents two nodes can receive a 0 if there is no relationship (e.g., has no connecting lines between the nodes) or either a +1 for a positive relationship (e.g., positive impact) or a −1 for a negative relationship (e.g., negative impact). As described previously in FIG. 6, a node (e.g., a health factor) has a positive impact if it increases the risk of the disease (e.g., another node) to which it points to with an edge (e.g., a line). A negative relationship (e.g., a negative impact) decreases the risk of the pointed disease.

Graph 708 is a portion of the selected nodes and edges from the initial directed graph 702. The edges in graph 708 are labeled to calculate the penalty. The edge between sbp and af is labeled $b_{kp}$. The letter "b" indicates Matrix B (e.g., matrix 706), "k" represents af and "p" represents sbp. The letter "w" in the label $w_{jk}$ represents the weight value for the relationship between af as indicated by the letter "k" and stroke as indicated by the letter "j". Therefore, $w_{jp}$ represents the weight value for the relationship between sbp and stroke. When estimating the weight value between sbp and stroke and the weight value between af and stroke, these estimations will be reflected by the relationship between sbp and af. For example, when there is no relationship between sbp and af, and $b_{kp}$ is 0, $w_{jk}$ and $w_{jp}$ are estimated separately. If $b_{kp}$ is +1, the penalty will be proportional to the absolute value of $w_{jk}-w_{jp}$. In order to lower the penalty, $w_{jk}-w_{jp}$ should be smaller. If $b_{kp}$ is −1, the penalty will proportional to the absolute value of $w_{jk}+w_{jp}$. In order to lower the penalty, $w_{jk}+w_{jp}$ should be smaller. That means $w_{jk}$ should be more different to $w_{jp}$ (e.g., one positive and one negative). The penalty is calculated using the equation 710.

More specifically, the penalty contains two parts. The first part (e.g., Matrix A or matrix 704) indicates the penalty for the non-existence of relationships in 702. "$a_{jk}$" means the value in $k^{th}$ row and the $j^{th}$ column in Matrix A (e.g., matrix 704). "$w_{jk}$" means the weight value that reflect the relationship between the $k^{th}$ factor and the $j^{th}$ target disease in Matrix A (e.g., matrix 704). The second part (e.g., Matrix B or matrix 706) indicates penalty for the co-existence of relationship between two factors and one target disease. "$b_{kp}$" means the value in the $k^{th}$ row and the $p^{th}$ column in Matrix B (e.g., matrix 706). The "$\lambda$" and "$\theta$" are parameters defined by knowledge to indicate the proportions of different part of the penalty. For example, the "$\lambda$" and "$\theta$" can be set as 0.5 and 0.5 respectively to allocate the equal importance of these two parts to the total penalty.

The multi-task learning structure 712 is a multi-task learning mechanism and can be depicted by an equation similar to equation 714 and adding the penalty(w,A,B) calculated from equation 710. Equation 714 is the equation of loss function of multi-task learning structure 712, which should be optimized to build the multi-task learning model. The letter "l" indicates the loss function. "$x_{(i)}$" means the values of factors and historical diseases of the $i^{th}$ patients. "$y_{ij}$" means the value of the $j^{th}$ target disease for the $i^{th}$ patients. "$w_j$" means the $j^{th}$ weights that reflect the relationship among all patients' factors and the $j_{th}$ target disease. The training process is to calculate proper weights based on given x and y to optimize the loss function "l". In order to utilize the knowledge based disease relationship from literature, the knowledge can be included into the loss function as "penalty" and can influence the training of weights by Matrix A (e.g., matrix 704) and Matrix B (e.g., matrix 706). The penalties are added to the loss function in order to adjust the training and final determination of the values of the weights. The first part of equation 714 can be, but is not limited to, a logistic regression function. The result is a treatment directed graph with weight values added to the edges connecting the nodes as shown in FIG. 8.

Figure 8:
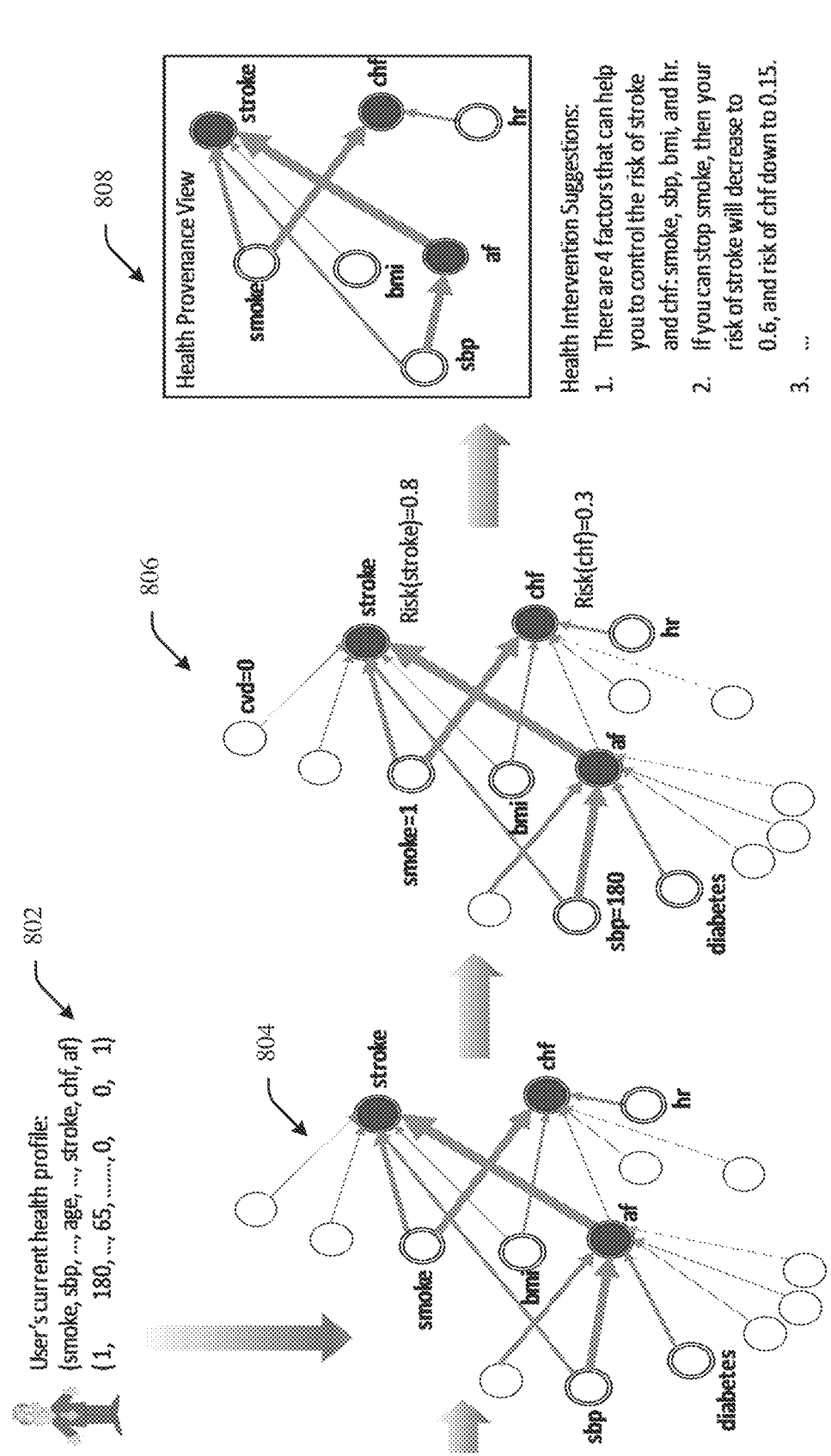
FIG. 8 illustrates a block diagram of an example, non-limiting health intervention suggestion generation facilitating provisioning a set of treatment suggestions in accordance with one or more embodiments described herein.

FIG. 8 illustrates a block diagram of an example, non-limiting health intervention suggestion generation in accordance with one or more embodiments described herein. The impact component 302 can apply the patient directed graph or user's current health profile 802 to the treatment directed graph 804 (e.g., generated by the machine learning component 202 as illustrated in FIG. 7) and calculate the current risk status (e.g., risk score) for the diseases for the patient as shown in directed graph 806. The impact component 302 can tag or mark all the variables (e.g., nodes) as controllable factors or uncontrollable factors based on knowledge. The impact component 302 can also tag the nodes as start nodes (e.g., the edge end with the arrow pointing away) or end nodes (e.g., the edge end with arrow pointing towards). Whether a node is a start node or end node depends on which node it is connected to and the edge that connects the two nodes. The impact component 302 can find all controllable nodes and calculate the risk scores from the controllable factors to the risk factors. Given a patient's data for a given risk factors, the impact component 302 can calculate the impact of the controllable factors (e.g. overeating) for a given risk factors (e.g., weight gain) and calculate the impact of a given risk factors (e.g., weight gain) for a given risks (e.g., diabetes).

The risk score calculation can be further incorporated in the treatment suggestions or health intervention suggestions 808 for the patient by the suggestion component 114. In this example, for the patient with the user's current health profile 802, there are four factors that can help control the risk of stroke and chf, which are smoke, sbp, bmi and hr (heart rate). Smoke is a controllable factor with impact values (e.g., weight values) that can reduce the risk scores to 0.6 and 0.15 for stroke and chf, respectively. If the patient quit smoking, the patient can reduce the risk of stroke to down to 0.6 and reduce the risk of chf down to 0.15.

More specifically, in this patient directed graph, values are added to all the nodes. For example, node "smoke" has a value of 1 and node "af" also has a value equal to 1. As illustrated in this example, this user has not gotten stroke and chf, so this patient directed graph can be utilized to predict the risk of stroke and chf for this user. As the weight values for the factors are known, the risk scores can be calculated for the target diseases. In this example, the calculated risk score is 0.8 for stroke and 0.3 for chf, respectively. The risk scores can be calculated using the expression, $$\{risk(chf), risk(stroke)\}=f(\{smoke=1, sbp=180, \ldots, age=65, \ldots\}, W).$$

Once the patient directed graph is completed, the health suggestions can be generated. The health provenance view (e.g., health intervention suggestions 808) is part of the patient directed graph. The nodes (e.g., health factors, diseases, etc.) that have an impact on the target diseases will be selected. For example, if the weight between factor x (e.g., represented by a node) and target disease y (e.g., represented by a node) is too small (e.g., can be filtered by a threshold), the impact of x can be ignored, and the node x will not be selected. In another example, if the value of x equals 0 (e.g., such as node "cvd" in this example), then in spite of its weight value (e.g., impact values), this node will also not be selected. A health provenance view (e.g., health intervention suggestions 808) can be generated with health intervention suggestions such as the one in this example that reads, "1. There are 4 factors that can help you to control the risk of stroke and chf: smoke, sbp, bmi, and hr. 2. If you can stop smoke, then your risk of stroke will decrease to 0.6, and risk of chf down to 0.15." In the health intervention suggestions number 2, the analysis is based on a calculation that replaces the value of smoke to 0:

$$\{risk'(chf), risk'(stroke)\}=f(\{smoke=0, sbp=180, \ldots, age=65, \ldots\}, W).$$

Figure 9:
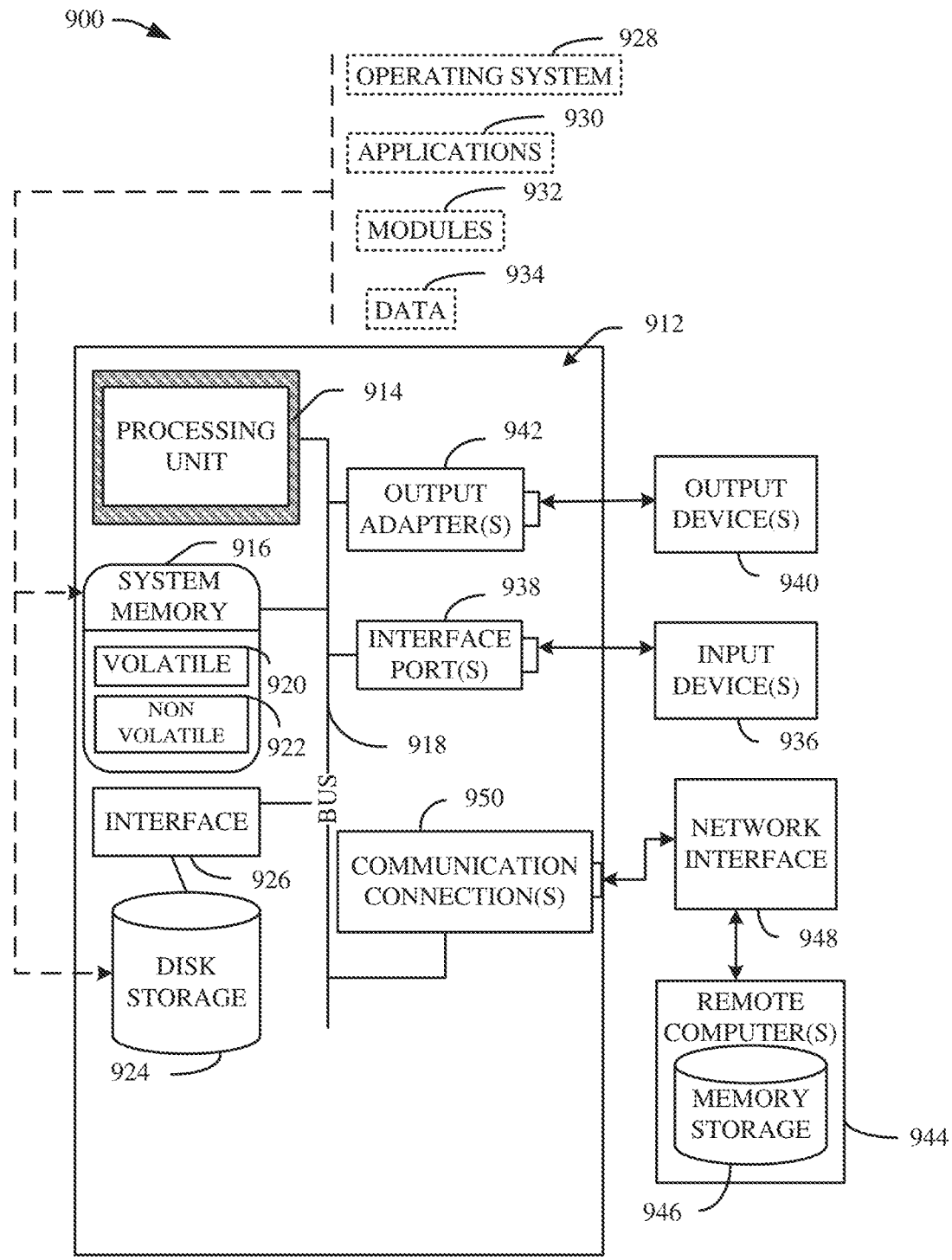
FIG. 9 illustrates a block diagram of an example, non-limiting operating environment in which one or more embodiments described herein can be facilitated.

In order to provide a context for the various aspects of the disclosed subject matter, FIG. 9 as well as the following discussion are intended to provide a general description of a suitable environment in which the various aspects of the disclosed subject matter can be implemented. FIG. 9 illustrates a block diagram of an example, non-limiting operating environment in which one or more embodiments described herein can be facilitated. Repetitive description of like elements employed in other embodiments described herein is omitted for sake of brevity.

With reference to FIG. 9, a suitable operating environment 900 for implementing various aspects of this disclosure can also include a computer 912. The computer 912 can also include a processing unit 914, a system memory 916, and a system bus 918. The system bus 918 couples system components including, but not limited to, the system memory 916 to the processing unit 914. The processing unit 914 can be any of various available processors. Dual microprocessors and other multiprocessor architectures also can be employed as the processing unit 914. The system bus 918 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 916 can also include volatile memory 920 and nonvolatile memory 922. The basic input/output system (BIOS), containing the basic routines to transfer information between elements within the computer 912, such as during start-up, is stored in nonvolatile memory 922. Computer 912 can also include removable/non-removable, volatile/non-volatile computer storage media. FIG. 9 illustrates, for example, a disk storage 924. Disk storage 924 can also include, but is not limited to, devices like a magnetic disk drive, floppy disk drive, tape drive, Jaz drive, Zip drive, LS-100 drive, flash memory card, or memory stick. The disk storage 924 also can include storage media separately or in combination with other storage media. To facilitate connection of the disk storage 924 to the system bus 918, a removable or non-removable interface is typically used, such as interface 926. FIG. 9 also depicts software that acts as an intermediary between users and the basic computer resources described in the suitable operating environment 900. Such software can also include, for example, an operating system 928. Operating system 928, which can be stored on disk storage 924, acts to control and allocate resources of the computer 912.

System applications 930 take advantage of the management of resources by operating system 928 through program modules 932 and program data 934, e.g., stored either in system memory 916 or on disk storage 924. It is to be appreciated that this disclosure can be implemented with various operating systems or combinations of operating systems. A user enters commands or information into the computer 912 through input device(s) 936. Input devices 936 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 914 through the system bus 918 via interface port(s) 938. Interface port(s) 938 include, for example, a serial port, a parallel port, a game port, and a universal serial bus (USB). Output device(s) 940 use some of the same type of ports as input device(s) 936. Thus, for example, a USB port can be used to provide input to computer 912, and to output information from computer 912 to an output device 940. Output adapter 942 is provided to illustrate that there are some output devices 940 like monitors, speakers, and printers, among other output devices 940, which require special adapters. The output adapters 942 include, by way of illustration and not limitation, video and sound cards that provide a means of connection between the output device 940 and the system bus 918. It should be noted that other devices and/or systems of devices provide both input and output capabilities such as remote computer(s) 944.

Computer 912 can operate in a networked environment using logical connections to one or more remote computers, such as remote computer(s) 944. The remote computer(s) 944 can be a computer, a server, a router, a network PC, a workstation, a microprocessor based appliance, a peer device or other common network node and the like, and typically can also include many or all of the elements described relative to computer 912. For purposes of brevity, only a memory storage device 946 is illustrated with remote computer(s) 944. Remote computer(s) 944 is logically connected to computer 912 through a network interface 948 and then physically connected via communication connection 950. Network interface 948 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 950 refers to the hardware/software employed to connect the network interface 948 to the system bus 918. While communication connection 950 is shown for illustrative clarity inside computer 912, it can also be external to computer 912. The hardware/software for connection to the network interface 948 can also include, for exemplary purposes only, internal and external technologies such as, modems including regular telephone grade modems, cable modems and DSL modems, ISDN adapters, and Ethernet cards.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
    a memory that stores computer executable components; and
    a processor, operably coupled to the memory, and that executes computer executable components stored in the memory, wherein the computer executable components comprise:
        a patient assessment component that generates a patient directed graph regarding two or more diseases associated with a patient;
        a treatment component that generates treatment directed graphs associated with a plurality of treatment regimens, wherein, in connection with generating respective treatment directed graphs, penalties are applied during weighting of respective regimens as a function of an associated confidence level, wherein the weighting is determined as a function of the associated confidence level based on machine learning;
        a matching component that identifies a treatment directed graph that corresponds to a patient directed graph regarding two or more diseases associated with the patient, wherein the matching component performs the identification based on a determination that the treatment directed graph has the health factors as those found in the patient directed graph, and wherein the treatment directed graph indicates two or more potential diseases relating to a set of the health factors of the patient;
  a suggestion component that outputs a set of treatment suggestions associated with the treatment directed graph that corresponds to the patient directed graph, wherein the outputting the set of treatment suggestions comprises:
    identification of an impact between controllable factors and the target disease;
    identification of previously output treatment suggestions associated with a second patient directed graph regarding two or more diseases associated with a second patient, wherein the patient directed graph and the second patient directed graph comprise one or more identical health factors;
    an outputting of the previously output treatment suggestions;
    an outputting of first information indicating a manner in which a selected health intervention concurrently impacts multiple diseases associated with the patient; and
    an outputting of second information indicating changes to respective quantifications of risks of the multiple diseases based on ceasing or continuing one or more of the controllable factors; and
  a machine learning component that extracts predictive relationships relating to diseases from literature, wherein the predictive relationships relating to diseases from literature have an associated weighted value,
    wherein a first penalty value is a first associated weighted value indicating no penalty will be applied between nodes during training wherein the determination not to apply the penalty is based on a determination that there is a predictive relationship between a first one of the multiple diseases and a second one of the multiple diseases, and
    wherein a second penalty value is a second associated weighted value indicating a penalty will be applied between the nodes during training wherein the determination to apply the penalty is based on a determination that there is no predictive relationship between the first one of the multiple diseases and the second one of the multiple diseases, wherein the first penalty value is less than the second penalty value.

2. The system of claim 1, wherein the patient assessment component collects patient data used by the system to generate the patient directed graph regarding the two or more diseases associated with the patient, wherein the two or more diseases are part of the same health domain.

3. The system of claim 1, wherein the patient assessment component identifies patient data used by the system to generate the patient directed graph regarding the two or more diseases associated with the patient.

4. The system of claim 1, wherein the treatment component receives structured health data and predictive relationships relating to diseases from literature used by the system to generate the treatment directed graphs associated with the plurality of treatment regimens.

5. The system of claim 1, wherein the predictive relationships relating to diseases from literature are learned concurrently.

6. The system of claim 1, further comprising an impact component that applies the patient directed graph to the treatment directed graph to identify one or more risk factors as one or more controllable factors or one or more uncontrollable factors and labels nodes in the patient directed graph as start nodes or end nodes.

7. The system of claim 6, wherein the impact component calculates an impact of the one or more controllable factors to the one or more risk factors.

8. The system of claim 1, wherein the first penalty value is 0 and the second penalty value is 1.

9. A computer-implemented method, comprising:
  generating, by a system operatively coupled to a processor, a patient directed graph regarding two or more diseases associated with a patient;
  generating, by the system, treatment directed graphs associated with a plurality of treatment regimens, wherein, in connection with generating respective treatment directed graphs, penalties are applied during weighting of respective regimens as a function of an associated confidence level, wherein the weighting is determined as a function of the associated confidence level based on machine learning;
  identifying, by the system, a treatment directed graph that corresponds to a patient directed graph;
  outputting, by the system, a set of treatment suggestions associated with the treatment directed graph that corresponds to the patient directed graph, wherein the set of treatment suggestions identifies an impact between controllable factors and a target disease, conveys a manner in which a selected health intervention concurrently impacts multiple diseases associated with the patient, and increases and decreases respective quantified risks of the multiple diseases based on ceasing or commencing one or more of the controllable factors;
  identifying, by the system, previously output treatment suggestions associated with a second patent directed graph regarding two or more diseases associated with a second patient, wherein the patient directed graph and the second patient directed graph comprise one or more identical health factors;
  outputting, by the system, the previously output treatment suggestions;
  extracting, by the system, predictive relationships relating to diseases from literature, wherein predictive relationships relating to diseases from literature have an associated weighted value,
    wherein a first penalty value is a first associated weighted value indicating no penalty will be applied between nodes during training wherein the determination not to apply the penalty is based on a determination that there is a predictive relationship between a first one of the multiple diseases and a second one of the multiple diseases, and
    wherein a second penalty value is a second associated weighted value indicating a penalty will be applied between the nodes during training wherein the determination to apply the penalty is based on a determination that there is no predictive relationship between the first one of the multiple diseases and the second one of the multiple diseases, wherein the first penalty value is less than the second penalty value.

10. The computer-implemented method of claim 9, further comprising identifying, by the system, patient data used by the system to generate the patient directed graph regarding the two or more diseases associated with the patient, wherein the two or more diseases are part of the same health domain.

11. The computer-implemented method of claim 9, wherein the predictive relationships relating to diseases from literature are learned concurrently.

12. The computer-implemented method of claim 9, further comprising applying, by the system, the patient directed graph to the treatment directed graph to identify one or more risk factors as one or more controllable factors or one or more uncontrollable factors and labels nodes in the patient directed graph as start nodes or end nodes.

13. The computer-implemented method of claim 12, further comprising calculating, by the system, an impact of the one or more controllable factors to the one or more risk factors.

14. A computer program product that facilitates determining a set of treatment suggestions, the computer program product comprising a non-transitory computer readable storage medium having program instructions embodied therewith, the program instructions executable by a processor to cause the processor to:
generate a patient directed graph regarding two or more diseases associated with a patient;
generate treatment directed graphs associated with a plurality of treatment regimens, wherein, in connection with generating respective treatment directed graphs, penalties are applied during weighting of respective regimens as a function of an associated confidence level, wherein the weighting is determined as a function of the associated confidence level based on machine learning;
identify a treatment directed graph that corresponds to a patient directed graph;
output a set of treatment suggestions associated with the treatment directed graph that corresponds to the patient directed graph, wherein the set of treatment suggestions identifies an impact between controllable factors and a target disease, conveys a manner in which a selected health intervention concurrently impacts multiple diseases associated with the patient, and changes respective quantified risks of the multiple diseases based on ceasing one or more of the controllable factors;
identify one or more previously output treatment suggestions associated with a second patient directed graph regarding two or more diseases associated with a second patient, wherein the patient directed graph and the second patient directed graph comprise one or more identical health factors;
output the previously output treatment suggestions; and
extract predictive relationships relating to diseases from literature, wherein predictive relationships relating to diseases from literature have an associated weighted value,
wherein a first penalty value is a first associated weighted value indicating no penalty will be applied between nodes during training wherein the determination not to apply the penalty is based on a determination that there is a predictive relationship between a first one of the multiple diseases and a second one of the multiple diseases, and
wherein a second penalty value is a second associated weighted value indicating a penalty will be applied between the nodes during training wherein the determination to apply the penalty is based on a determination that there is no predictive relationship between the first one of the multiple diseases and the second one of the multiple diseases, wherein the first penalty value is less than the second penalty value.

15. The computer program of claim 14, wherein the program instructions are further executable to cause the processor to:
identify patient data used by the system to generate the patient directed graph regarding the two or more diseases associated with the patient, wherein the two or more diseases are part of the same health domain.

16. The computer program product of claim 14, wherein the program instructions are further executable to cause the processor to:
apply the patient directed graph to the treatment directed graph to identify one or more risk factors as one or more controllable factors or one or more uncontrollable factors and label nodes in the patient directed graph as start nodes or end nodes.

17. The computer program product of claim 16, wherein the program instructions are further executable to cause the processor to:
calculate an impact of the one or more controllable factors to the one or more risk factors.

* * * * *